United States Patent [19]

Biere et al.

[11] Patent Number: 4,457,927
[45] Date of Patent: Jul. 3, 1984

[54] PYRIDO[2,1-B]QUINAZOLINONE DERIVATIVES AND THE PREPARATION AND USE THEREOF

[75] Inventors: Helmut Biere; Joachim-Friedrich Kapp; Irmgard Böttcher, all of Berlin, Fed. Rep. of Germany

[73] Assignee: Schering, Aktiengesellschaft, Berlin and Bergkamen, Fed. Rep. of Germany

[21] Appl. No.: 452,009

[22] Filed: Dec. 22, 1982

Related U.S. Application Data

[63] Continuation of Ser. No. 316,577, Oct. 30, 1981, abandoned, which is a continuation of Ser. No. 86,103, Oct. 18, 1979, abandoned.

[30] Foreign Application Priority Data

Oct. 18, 1978 [DE] Fed. Rep. of Germany ....... 2845766

[51] Int. Cl.³ ............... C07D 471/04; A61K 31/505
[52] U.S. Cl. ............................. 424/245; 544/225; 544/252; 424/251
[58] Field of Search ............... 424/251, 245; 544/225, 544/252

[56] References Cited

U.S. PATENT DOCUMENTS

| | | | |
|---|---|---|---|
| 3,415,834 | 12/1968 | Hoffman | 544/252 |
| 4,033,961 | 7/1977 | Schwender | 544/252 |
| 4,066,767 | 1/1978 | Schwender | 544/252 |
| 4,083,980 | 4/1978 | Schromm et al. | 544/252 |

FOREIGN PATENT DOCUMENTS

| | | | |
|---|---|---|---|
| 2812586 | 9/1978 | Fed. Rep. of Germany | 544/252 |
| 2812585 | 9/1978 | Fed. Rep. of Germany | 544/252 |

OTHER PUBLICATIONS

Biere Chemical Abs. 90, 204131m (1979).
Schromm, Chem. Abs. 87, 117898.

*Primary Examiner*—Mark L. Berch
*Attorney, Agent, or Firm*—Millen & White

[57] ABSTRACT

Pyrido[2,1-b]quinazolinones of the formula

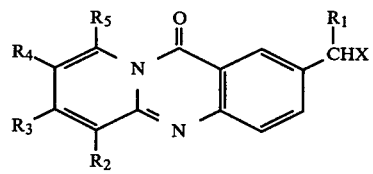

wherein
X is cyano, hydroxyamidocarbonyl, carbamoyl, 5-tetrazolyl, carboxy, carboxy in the form of a salt thereof with a physiologically compatible base, carboxy esterified with a physiologically acceptable alcohol or carboxy amidated with a physiologically acceptable amine;
$R_1$ is hydrogen or methyl; and
$R_2$ through $R_5$ are independently each hydrogen, halogen, alkyl of 1–4 carbon atoms, trifluoromethyl, carboxy, thiocyano, methylthio, methylsulfinyl, methylsulfonyl, methylsulfonimidoyl or methylsulfonamido with the proviso that two or three of the groups $R_2$ through $R_5$ are hydrogen; or a salt thereof with a physiologically acceptable acid or base;

possess valuable pharmacological properties.

12 Claims, No Drawings

PYRIDO[2,1-B]QUINAZOLINONE DERIVATIVES AND THE PREPARATION AND USE THEREOF

This is a continuation of application Ser. No. 316,577 filed Oct. 30, 1981 which is a continuation of U.S. Ser. No. 086,103 filed Oct. 18, 1979, both now abandoned.

BACKGROUND OF THE INVENTION

The present invention relates to pyrido[2,1-b]quinazolinone derivatives, a process for the preparation thereof, and the use thereof as active medicinal ingredients.

SUMMARY OF THE INVENTION

It is an object of this invention to provide new compounds which are pharmacologically active.

Upon further study of the specification and appended claims, further objects and advantages of this invention will become apparent to those skilled in the art.

These objects have been attained by providing pyrido[2,1-b]quinazolinones of Formula I

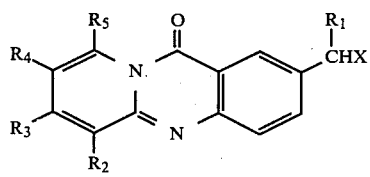

wherein

X is cyano, hydroxyamidocarbonyl, carbamoyl, 5-tetrazolyl, carboxy, carboxy in the form of a salt thereof with a physiologically compatible base, carboxy esterified with a physiologically acceptable alcohol or carboxy amidated with a physiologically acceptable amine;

$R_1$ is hydrogen or methyl; and $R_2$ through $R_5$ are independently each hydrogen, halogen, alkyl of 1-4 carbon atoms, trifluoromethyl, carboxy, thiocyano, methylthio, methylsulfinyl, methylsulfonyl, methylsulfonimidoyl or methylsulfonamido with the proviso that two or three of the groups $R_2$ through $R_5$ are hydrogen; or a salt thereof with a physiologically acceptable acid or base.

DETAILED DISCUSSION

The present invention includes, as the case may be, the racemic pyrido[2,1-b]quinazolinone derivatives of Formula I, as well as to the optically active antipodes thereof.

Examples of physiologically compatible salts of the carboxy group X of Formula I include the alkali and alkaline earth metal salts, such as the sodium salt or the calcium salt, the ammonium salt, the copper(II) salt and the methylglucamine salt, as well as the salts with amino acids, e.g., the natural amino acids.

Physiologically acceptable alcohols with which the carboxy group X of Formula I can be esterified include, for example, straight-chain, branched or cyclic, saturated or unsaturated hydrocarbon alcohols, preferably of 1-12, and especially of 1-6, carbon atoms which can also be interrupted by an oxygen atom or a nitrogen atom, and which can be substituted by additional hydroxy groups, amino groups or carboxy groups, e.g., alkanols, (especially those of 1-6 carbon atoms), alkenols, alkynols, cycloalkanols, cycloalkylalkanols, phenylalkanols, phenylalkenols, alkanediols, hydroxycarboxylic acids, aminoalkanols, or $C_{1-4}$ alkylaminoalkanols and di-$C_{1-4}$-alkylaminoalkanols.

Such alcohols suitable for the esterification of the carboxy group include, for example, those having a residue of methylcarboxymethyl, ethyl, 2-hydroxyethyl, 2-methoxyethyl, 2-aminoethyl, 2-dimethylaminoethyl, 2-carboxyethyl, propyl, allyl, cyclopropylmethyl, isopropyl, 3-hydroxypropyl, propynyl, 3-aminopropyl, butyl, sec-butyl, tert-butyl, 2-butyl, cyclobutyl, pentyl, isopentyl, tert-pentyl, 2-methylbutyl, cyclopentyl, hexyl, cyclohexyl, cyclo-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, undecyl and dodecyl. Alcohols suitable for esterification include also those forming labile esters, i.e., esters which can be cleaved under phsyiological conditions, e.g., 5-hydroxyindan, acyloxymethanols, especially acetoxymethanol, pivaloyloxymethanol, 5-indanyloxycarbonylmethanol, glycolic acid, dialkylaminoalkanols, especially dimethylaminopropanol, as well as hydroxyphthalide.

Physiologically acceptable amines with which the carboxy group can be amidated include preferably $C_{1-6}$ alkylamines, di-$C_{1-6}$-alkylamines, $C_{1-6}$ alkanolamines, di-$C_{1-6}$-alkanolamines and 5- or 6-membered N-heterocycles which optionally may also include one additional O, N or S hetero atom. Examples of such suitable amines include methylamine, ethylamine, isopropylamine, ethanolamine, dimethylamine diethylamine, diethanolamine, pyrrolidine, piperidine, morpholine and N-methylpiperazine.

Halogen atoms for $R_2$ are F, Cl, Br and I. Suitable alkyl groups or moieties for all radicals include methyl, ethyl, propyl, isopropyl, n-butyl, isobutyl, sec-butyl, tert-butyl, n-pentyl, isopentyl, tert-pentyl, n-hexyl, isohexyl, etc.

Salts of the pyrido[2,1-b]quinazolinone derivatives of Formula I with physiologically acceptable bases include, for example, alkali metal salts or alkaline earth metal salts, such as the sodium salts or calcium salts, ammonium salts, copper(II) salts, methylglucamine salts, piperazine salts, or the salts of these compounds with amino acids.

Examples of suitable physiologically acceptable pyrido[2,1-b]quinazolinium salts of the compounds of Formula I with acids include the hydrochlorides, hydrobromides, sulfates, phosphates, oxalates, maleates, tartrates and citrates.

The compounds of Formula I may be prepared by several processes. For example, they may be prepared by (1) condensing a pyridine derivative of Formula II with a phenyl derivative of Formula III

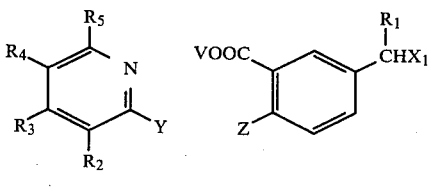

wherein $R_1$ through $R_5$ are as defined above,
$X_1$ is cyano, carboxy or alkoxycarbonyl,
V is hydrogen or alkyl,
Y is amino when Z is halogen, or
Y is halogen or an esterified or etherified hydroxy group when Z is amino, optionally, saponifying the thus-produced cyano compounds or alkoxycarbonyl compounds or converting them into the corresponding carbamoyl or tetrazolyl compounds, optionally, separating the racemic carboxylic acids into their optical antipodes and/or converting the carboxylic acids or reactive derivatives thereof into their salts, esters, amides, hydroxamic acids, or tetrazolyl derivatives, or, optionally, reacting the thus-obtained pyrido[2,1-b]quinazolinone derivatives with physiologically acceptable acids or bases.

This process is conducted under conventional conditions well-known to those skilled in the art (Ullmann reaction). Preferred starting compounds for this process are those pyridine derivatives of Formula II wherein Y is amino, chlorine, bromine, alkoxy of 1-4 carbon atoms, trimethylsilyloxy, methanesulfonyloxy or p-toluenesulfonyloxy. The phenyl derivatives of Formula III used as the starting compounds preferably are those wherein V is hydrogen or alkyl of 1-4 carbon atoms and Z is amino, chlorine, or bromine. Preferred alkoxycarbonyl groups $X_1$ of the compounds of Formula III are those wherein the alkyl is of 1-4 carbon atoms.

The reaction is preferably conducted by heating the reactants—optionally, in a high-boiling solvent (e.g., ethylene glycol, ethylene glycol monomethyl ether, ethylene glycol monobutyl ether or ethylene glycol diethyl ether)—in the presence of a base with copper or zinc catalysts to 100°–250° C. Suitable bases include, for example, alkali metal carbonates, (e.g., sodium carbonate or potassium carbonate) or high-boiling tertiary amines (e.g., N-ethylmorpholine, N-ethylpiperidine, etc.). Suitable copper or zinc catalysts include, for example, zinc(II) chloride, copper powder, copper(I) oxide, copper(II) oxide, copper(II) chloride, copper(II) sulfate, or, in particular, copper(II) bromide and copper(I) bromide.

Another process for preparing the compounds of Formula I(a)

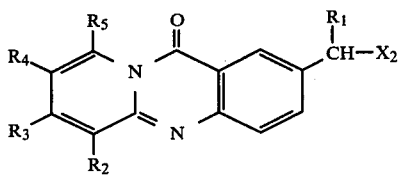

wherein
$R_1$ through $R_5$ are as defined above, and
$X_2$ is carboxy, a salt thereof with a physiologically compatible base, an ester thereof with a physiologically acceptable alcohol or an amide thereof with a physiologically acceptable amine, comprises (2) hydrolyzing a nitrile of Formula I(b)

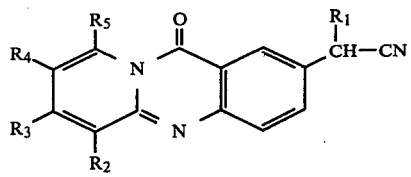

wherein $R_1$ through $R_5$ are as defined above.

This process also is conducted under conventional conditions well-known to a person skilled in the art. For example, using a strong mineral acid (such as hydrochloric acid or sulfuric acid) or a strong base (such as aqueous sodium hydroxide solution or potassium hydroxide solution), the nitriles of Formula I(b) can be hydrolyzed partially to the corresponding amides or, under stricter conditions, well known by the artisan, to the corresponding carboxylic acids. The hydrolysis is customarily effected at a reaction temperature of 20°–160° C.

For this reaction, the aqueous mineral acid or the base per se can also serve as the solvent. However, on the other hand, it is also possible to conduct the reaction in the presence of polar solvents, e.g., lower alcohols (e.g., methanol, ethanol, isopropanol, etc.), carboxylic acids (e.g., acetic acid, propionic acid, etc.), polar ethers (e.g., glycol monomethyl ether, dioxane, tetrahydrofuran, etc.) or dipolar aprotic solvents (e.g., dimethyl sulfoxide, etc.).

The starting compounds of Formula I(a) can be prepared using processes Numbers 1 above or 5 or 6 below.

A further process for preparing the compounds of Formula I(a) comprises (3) decarboxylating a carboxylic acid of Formula IV

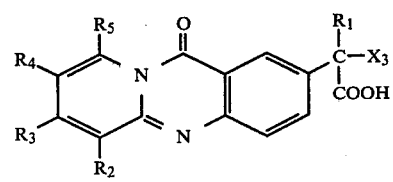

wherein
$R_1$ through $R_5$ are as defined above, and
$X_3$ is cyano, carboxy, or $C^{1-6}$ alkoxycarbonyl and, optionally, hydrolyzing the product.

This process is likewise conducted under conventional conditions well-known to those skilled in the art. It can be conducted by thermal heating of the malonic acid derivatives of Formula IV to 50°–150° C., whereby the decarboxylation can be accomplished in the absence of a solvent, or also in the presence of a high-boiling solvent (such as xylene, chlorobenzene, or decahydronaphthalene, etc.).

The starting compounds of Formula IV used for this version of the process can be prepared, for example, as follows: Pyrido[2,1-b]quinazolinone derivatives of Formula I wherein $R_1$ is hydrogen and X is cyano or alkoxycarbonyl may be reacted in diethyl carbonate with sodium hydride. The excess solvent is removed by distillation, and the thus-obtained crude product can then optionally be methylated in dimethylformamide with methyl iodide and sodium hydride.

In still another process, the compounds of Formula I can be prepared by (4) reacting a compound of Formula V

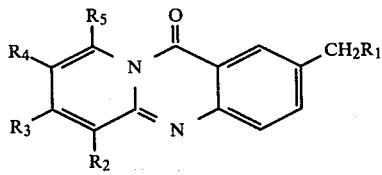

wherein $R_1$ through $R_5$ are as defined above, with carbon dioxide or a $C^{1-6}$ alkyl ester of chlorocarbonic acid, in the presence of an alkali metal hydride, alkali metal amide, or alkali metal alcoholate and optionally, separating the racemic carboxylic acids into their optical antipodes and/or converting the carboxylic acids or reactive derivatives thereof into their salts, esters or amides and, optionally, reacting the thus-obtained pyrido[2,1-b]quinazolinone derivatives with physiologically acceptable acids.

This process also is conducted under conventional conditions familiar to those skilled in the art. Thus, it is possible, for example, to react the compounds of Formula V in an inert solvent (e.g., dioxane, tetrahydrofuran, glycol dimethyl ether, etc.) with lithium diisopropylamide and carbon dioxide. On the other hand, it is also possible, for example, to react the compounds of Formula I in an inert solvent (e.g., dioxane, tetrahydrofuran, glycol dimethyl ether, etc.) with potassium hydride and the ethyl ester of chlorocarbonic acid. These reactions are generally conducted at $-50°-+100°$ C.

The starting compounds of Formula V required for this version of the process can be prepared, for example, according to process 1 above.

The optional procedures mentioned in processes 1-4 can be conventionally conducted, for example, under the conditions described in DOS [German Unexamined Laid-Open Application] No. 2,431,292.

Another process for preparing compounds of Formula I(b)

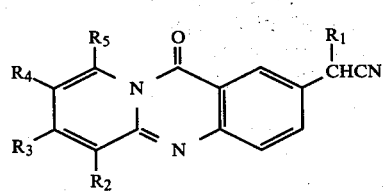

wherein $R_1$ through $R_5$ are as defined above, comprises (5) reacting a compound of Formula VI

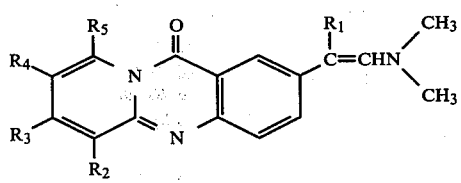

wherein $R_1$ through $R_5$ are as defined above, with hydroxylamino-O-sulfonic acid.

The process 5 of this invention has also been disclosed heretofore. It can be conducted by reacting the compounds of Formula VI in an aqueous solution or suspension, optionally in the further presence of a polar solvent such as methanol, ethanol, dioxane, tetrahydrofuran, dimethylformamide, or hexamethylphosphoric triamide, etc. with an excess of hydroxylamine-O-sulfonic acid (1.2-5 moles/mole of starting compound) at a reaction temperature of 20°-80° C. The amount of solvent generally is 500-10,000 wt.% based on the amount of compound of Formula VI. The reaction time is generally 1-24 hours.

The starting compounds of Formula VI required for this process can be obtained, for example, from compounds of Formula I wherein X is hydrogen, by heating them, optionally with the addition of dimethylformamide as a solvent, with an aminal ester, e.g., bis(dimethylamino)-tert-butoxymethane or with dimethylformamide acetals, e.g., dimethylformamide dimethylacetal, to 100°-150° C.

Another process for preparing the compounds of Formula I(b), comprises (6) reacting a compound of Formula VII

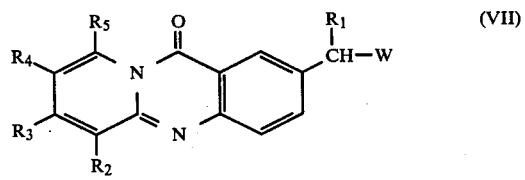

wherein $R_1$ through $R_5$ are as defined above and

W is chlorine, bromine, iodine or methanesulfonyloxy, with an alkali metal cyanide.

This process of this invention can be conducted under conventional conditions ordinarily employed for exchanging a halogen atom against a cyano group. This reaction is preferably effected in a protonic solvent (such as methanol, ethanol, isopropanol, etc.) or a dipolar, aprotic solvent (such as dimethylformamide, N-methylacetamide, N-methylpyrrolidone, acetonitrile, dimethyl sulfoxide, hexamethylphosphoric triamide, etc.). A preferred alkali metal cyanide for this reaction is sodium cyanide or potassium cyanide. In this reaction, the yield of product can frequently be increased by conducting the reaction in the presence of a crown ether (for example dibenzo-18-crown-6).

The preparation of the starting compounds of Formula VII is described in the examples herein.

Another process for preparing the compounds of Formula I(c)

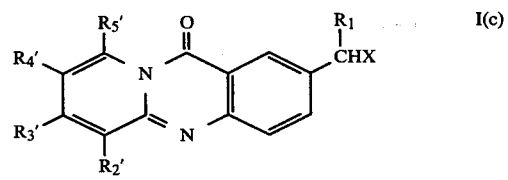

wherein

X and $R_1$ are as defined for Formula I and $R'_2$ through $R'_5$ are hydrogen, methylsulfinyl, methylsulfonyl and/or methylsulfonimidoyl, with the proviso that two or three of the groups $R'_2$ through $R'_5$ are hydrogen, (7) comprises oxidizing the corresponding methylthio compounds of Formula I and, optionally, reacting the thus-obtained methylsulfinyl compounds of Formula I(c) with alkali metal azides.

The oxidation (7) of the thio compounds to the sulfoxides or sulfones of Formula I is conducted according to known operating methods. In this reaction, suitable oxidizing agents include, for example, peracids, such as peracetic acid, perbenzoic acid, or m-chloroperbenzoic acid, etc., hydrogen peroxide, halogens, such as chlorine, bromine or iodine, tetra- to heptavalent metal oxides or metal salts, such as lead(IV) oxide, manganese(IV) oxide, chromium(VI) oxide, cerium(IV) sulfate, potassium chromate, potassium dichromate, potassium permanganate, etc., or oxidizing halogen compounds, such as sodium periodate, N-bromosuccinimide, N-chlorosuccinimide, or sodium hypochlorite, etc.

If hydrogen peroxide or metal oxides or metal salts are used for this oxidation, it is advantageous to conduct the oxidation in the presence of an acid. Suitable acids include mineral acids, such as hydrogen chloride or sulfuric acid, or lower carboxylic acids, such as acetic acid or propionic acid.

Suitable solvents for this reaction include protonic as well as aprotic inert solvents. Suitable are, for example, lower carboxylic acids, such as acetic acid or propionic acid, tertiary alcohols, such as tert-butanol, ketones, such as acetone, methyl ethyl ketone, or cyclohexanone, ethers, such as diethyl ether, diisopropyl ether, tetrahydrofuran, dioxane, or glycol dimethyl ether, hydrocarbons, such as benzene or toluene, or chlorinated hydrocarbons, such as methylene chloride, chloroform, carbon tetrachloride, tetrachloroethane or chlorobenzene. For producing sulfones of Formula I, the preferred solvent is acetic acid. The sulfoxides are preferably produced in acetone as the solvent.

The optionally following reaction of the methylsulfinyl compounds with alkali metal azides likewise takes place according to methods known per se, such as, for example, by reacting the compounds in the presence of acids, such as sulfuric acid, phosphoric acid, or polyphosphoric acid, with sodium azide.

The following pyrido[2,1-b]quinazolinone derivatives can be produced, for example, using the processes of this invention:
2-(8-bromo-6-methyl-11-oxo-11H-pyrido[2,1-b]quinazolin-2-yl)propionic acid,
2-(8-bromo-9-methyl-11-oxo-11H-pyrido[2,1-b]quinazolin-2-yl)propionic acid,
2-(8-chloro-7-methyl-11-oxo-11H-pyrido[2,1-b]quinazolin-2-yl)propionic acid,
2-(8-chloro-9-methyl-11-oxo-11H-pyrido[2,1-b]quinazolin-2-yl)propionic acid,
2-(8-chloro-7-trifluoromethyl-11-oxo-11H-pyrido[2,1-b]quinazolin-2-yl)propionic acid,
2-(8-bromo-11-oxo-11H-pyrido[2,1-b]quinazolin-2-yl)propionic acid methyl ester,
2-(8-chloro-11-oxo-11H-pyrido[2,1-b]quinazolin-2-yl)propionic acid methyl ester,
2-(8-fluoro-11-oxo-11H-pyrido[2,1-b]quinazolin-2-yl)propionic acid methyl ester,
2-(8-mesylamino-11-oxo-11H-pyrido[2,1-b]quinazolin-2-yl)propionic acid methyl ester, and
8-bromo-11-oxo-11H-pyrido[2,1-b]quinazoline-2-acetonitrile.

The pyrido[2,1-b]quinazolinone derivatives of Formula I are pharmacologically active compounds and/or can serve as intermediates for the production of such compounds. The pharmacologically effective compounds are especially distinguished by antiphlogistic, antipyretic, analgetic and antiallergic effects in patients, e.g., mammals including humans. Moreover, these compounds cause, in vitro, a pronounced phosphodiesterase inhibition. Gastric compatibility of the effective pyrido[2,1-b]quinazolinone derivatives is relatively high; their toxicity is relatively low.

The pharmacologically active compounds are suitable, in combination with the vehicles customary in galenic pharmacy, for example, for the treatment of acute and chronic inflammatory processes, polyarthritis, neurodermitis, bronchial asthma, hay fever and other indications as dismenorrhoe and sick headache.

The drug specialties are prepared in conventional fashion by converting the active agents together with suitable additives, carrier and flavor-ameliorating agents, into the desired forms of application, such as tablets, dragees, capsules, solutions, inhalants, etc.

For example, the pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Suitable for oral administration are, in particular, tablets, dragees, and capsules containing, for example, 5-500 mg of active ingredient and 50 mg to 2 g of pharmacologically inert vehicles, such as, for example, lactose, amylose, talc, gelatin, magnesium stearate and similar materials, as well as the customary additives.

Typical dosages are 1 to 500 mg/kg of body weight/day for use as an antiphlogistic, antipyretic or antiallergic agent. The administration is fully conventional e.g. in analogy to that for indomethacin, naproxene or ibuprophene.

Some of the compounds of the general formula I, e.g. those wherein X represents a cyano group are also valuable intermediates for the production of other compounds of the general formula I as mentioned above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

($a_1$) A solution of 15.1 g. of 2-amino-5-methylbenzoic acid in 200 ml. of ethylene glycol monobutyl ether is combined with 7.6 g. of pulverized potassium carbonate, 15 g. of N-ethylmorpholine, 28 g. of 2,5-dibromopyridine, and 1.8 g. of copper(II) bromide and stirred under argon for 6 hours at 180°. After the solvent has been distilled off under a water-jet aspirator vacuum, the residue is taken up in 1 l. of ethyl acetate and washed first with 1N acetic acid and then with sodium bicarbonate solution. The organic phase is concentrated, and the residue is recrystallized from chloroform, thus obtaining 15.2 g. of 8-bromo-2-methyl-11H-pyrido[2,1-b]quinazolin-11-one, m.p. 204°.

($a_2$) A solution of 1.7 g. of 2-chloro-5-methylbenzoic acid in 30 ml. of diethylene glycol dimethyl ether is combined with 1.5 g. of N-ethylmorpholine, 0.7 g. of pulverized potassium carbonate, 100 mg. of copper(II) bromide, and 2 g. of 2-amino-5-bromopyridine. The mixture is heated under nitrogen for 14 hours to 160°. After the solvent has been distilled off under vacuum, the reaction mixture is worked up analogously to ($a_1$), thus obtaining 1.2 g. of 8-bromo-2-methyl-11H-pyrido[2,1-b]quinazolin-11-one.

(b) A solution of 14.8 g. of 8-bromo-2-methyl-11H-pyrido[2,1-b]quinazolin-11-one in 500 ml. of carbon tetrachloride is combined with 11 g. of bromosuccinimide and 0.5 g. of azobisisobutyronitrile and irradiated with a 500 watt lamp, during which step the solution boils under reflux. After concentration of the solution, the residue is taken up in about 2 l. of chloroform, the organic phase washed with water, and after the solvent has been distilled off the yield is 18 g. of 8-bromo-2-bromomethyl-11H-pyrido[2,1-b]quinazolin-11-one, m.p. 208° (toluene).

($c_1$) 3.7 g. of 8-bromo-2-bromomethyl-11H-pyrido[2,1-b]quinazolin-11-one is added to a solution of 1.5 g. of sodium cyanide, 0.2 g. of potassium iodide, 3 ml. of water, and 50 ml. of ethanol. The mixture is refluxed for 15 minutes. After cooling, the thus-formed nitrile is crystallized; this product is vacuum-filtered, washed with water and a small amount of ethanol, and recrystallized from acetonitrile, thus obtaining 2.2 g. of 8-bromo-11-oxo-11H-pyrido[2,1-b]quinazoline-2-acetonitrile, m.p. 240°.

($c_2$) A solution of 17.3 g. of 8-bromo-2-bromomethyl-11H-pyrido[2,1-b]quinazolin-11-one in 500 ml. of chloroform is combined with a previously prepared complex from 3.1 g. of potassium cyanide and 16.9 g. of dibenzo-18-crown-6, as well as another 3.1 g. of potassium cyanide and refluxed for 30 minutes. Then the reaction mixture is agitated overnight at room temperature. The solution is then chromatographed with toluene over a silica gel column. Yield: 8.5 g. of 8-bromo-11-oxo-11H-pyrido[2,1-b]quinazoline-2-acetonitrile, m.p. 240° (tetrahydrofuran-water).

(d) A solution of 41.7 g. of concentrated sulfuric acid and 23 ml. of water is combined with 4 g. of 8-bromo-11-oxo-11H-pyrido[2,1-b]quinazoline-2-acetonitrile and the mixture is stirred for 3 hours at 120°. After cooling the solution is poured into a mixture of 400 ml. of ice water and set at pH 4-5 with sodium acetate, thus obtaining a crystallized product of 3.9 g. of 8-bromo-11-oxo-11H-pyrido[2,1-b]quinazoline-2-acetic acid, m.p. 271° (dimethylformamide-water).

EXAMPLE 2

(a) A solution of 3.8 g. of 8-bromo-11-oxo-11H-pyrido[2,1-b]quinazoline-2-acetonitrile in 75 ml. of diethyl carbonate is combined with 1.2 g. of sodium hydride dispersion (50%) and refluxed for 2 hours. After the solvent has been distilled off, the residue is taken up in 50 ml. of dimethylformamide and mixed at 0° with 3.5 g. of methyl iodide. The mixture is stirred for 1 hour at 0° and then overnight at room temperature. After concentration under a high vacuum, the oily residue is combined with 250 ml. of 1N acetic acid as well as 250 ml. of water, and the organic material is extracted with ethyl acetate. The crude product is recrystallized from ethanol, thus obtaining 2.5 g. of 2-cyano-2-(8-bromo-11-oxo-11H-pyrido[2,1-b]quinazolin-2-yl)propionic acid ethyl ester, m.p. 156°.

(b) A mixture of 1 g. of 2-cyano-2-(8-bromo-11-oxo-11H-pyrido[2,1-b]quinazolin-2-yl)propionic acid ethyl ester, 4 ml. of water, and 3 ml. of sulfuric acid (concentrated) is stirred for 3 hours at 120° (bath temperature). After cooling, the mixture is diluted with ice water and extracted with chloroform. The residue is recrystallized from ethanol, thus producing 0.5 g. of 2-(8-bromo-11-oxo-11H-pyrido[2,1-b]quinazolin-2-yl)propionic acid, m.p. 246°.

EXAMPLE 3

(a) A solution of 2.1 g. of 2-(4-amino-3-carboxyphenyl)propionic acid in 5 ml. of ethylene glycol monobutyl ether is stirred with 1.4 g. of pulverized potassium carbonate and 1.2 g. of N-ethylmorpholine for 0.5 hour at room temperature. Then 3.0 g. of 2,5-dibromopyridine and 150 mg. of copper(II) bromide are added thereto, and the mixture is heated under nitrogen for 7 hours to 180° (bath temperature). After the solvent has been removed by distillation under vacuum, the residue is dissolved in ethyl acetate and washed with dilute acetic acid. After acid-base extraction, the organic acid fraction is recrystallized from ethanol, thus obtaining 1.5 g. of 2-(8-bromo-11-oxo-11H-pyrido[2,1-b]quinazolin-2-yl)propionic acid, m.p. 251° (dimethylformamide-water).

(b) The starting material, 2-(4-amino-3-carboxyphenyl)propionic acid and/or the ester thereof is prepared as follows:

($b_1$) A solution of 35.7 g. of chloral hydrate in 480 ml. of water is combined with 36.9 g. of sodium sulfate, 38.6 g. of 2-(4-aminophenyl)propionic acid ethyl ester (prepared according to literature, G. Nannini et al., "Arzneimittelforschung [Drug Research] 23: 1090 [1973]), 120 ml. of water, 17 ml. of concentrated hydrochloric acid and with a solution of 43.9 g. of hydroxylammonium chloride in 200 ml. of water. The reaction mixture is heated gradually to boiling over a period of 45 minutes, then maintained at the boiling point for 10 minutes, and cooled off. The product, which separates in an oily form, is taken up in ethyl acetate and washed with water. After acid-base separation, the organic acid fraction is concentrated and recrystallized from acetonitrile, thus obtaining 25 g. of 2-[4-(2-hydroxyimino)acetamidophenyl]propionic acid, m.p. 163°.

($b_2$) 13 g. of 2-[4-(2-hydroxyimino)acetamidophenyl]-propionic acid is introduced in incremental portions into 55 g. of sulfuric acid (density 1.84), the latter having been preheated to 50°. During this step, the temperature of 70° is attained. After the compound has been added, the mixture is heated for 10 minutes to 80° and then poured into 300 ml. of ice water and extracted with ethyl acetate. Recrystallization from acetonitrile yields 10 g. of 2-(5-isatinyl)propionic acid, m.p. 224°.

($b_3$) During a time period of 20 minutes, 2.9 g. of hydrogen peroxide (30%) is added dropwise to a solution of 2.2 g. of 2-(5-isatinyl)propionic acid in 22 ml. of water and 3 ml. of 32% sodium hydroxide solution; the reaction mixture is then stirred for another 20 minutes. After the mixture has been acidified with 2N hydrochloric acid (pH 2-3), the organic material is extracted with ethyl acetate and finally recrystallized from acetonitrile, thus producing 1.8 g. of 2-(4-amino-3-carboxyphenyl)propionic acid, m.p. 179°.

($b_4$) 3 g. of 2-(4-amino-3-carboxyphenyl)propionic acid is dissolved in 500 ml. of methanolic hydrochloric acid (about 3%) and allowed to stand for 2 days at room temperature. After concentration, the residue is taken up in ethyl acetate, washed with sodium bicarbonate solution, and recrystallized, thus obtaining 2.8 g. of 2-(4-amino-3-carboxyphenyl)propionic acid methyl ester, m.p. 151° (acetonitrile).

EXAMPLE 4

(a) Under the conditions of Example 3(a), 2-(8-chloro-11-oxo-11H-pyrido[2,1-b]quinazolin-2-yl)propionic acid, m.p. 234°, is obtained from 2-bromo-5-chloropyridine and 2-(4-amino-3-carboxyphenyl)propionic acid.

(b) The starting material 2-bromo-5-chloropyridine is prepared analogously to methods know from the literature as follows:

17 ml. of bromine is added to a solution of 14 g. of 2-amino-5-chloropyridine in 30 ml. of water and 45 ml. of hydrobromic acid (63% in water); the mixture is cooled to 0°. Under temperature control, a solution of 21 g. of sodium nitrite in 30 ml. of water is added dropwise at such a rate that the temperature of the mixture does not exceed 5°. Thereafter, the mixture is combined under cooling with a solution of 45 g. of sodium hydroxide in 115 ml. of water. The thus-precipitated crystals are vacuum-filtered, washed with water, and recrystallized first from acetone and then once again from ethanol. Yield: 10 g. of 2-bromo-5-chloropyridine, m.p. 68°.

EXAMPLE 5

(a) Under the conditions described in Example 3(a), the methyl ester of 2-(6-chloro-11-oxo-11H-pyrido[2,1-b]quinazolin-2-yl)propionic acid is obtained from 2,3-dichloropyridine and 2-(4-amino-3-carboxyphenyl)propionic acid methyl ester.

(b) The above ester product is converted into 2-(6-chloro-11-oxo-11H-pyrido[2,1-b]quinazolin-2-yl)propionic acid by heating with dilute sodium hydroxide solution.

EXAMPLE 6

Under the conditions of Example 3(a), 2-(8-fluoro-11-oxo-11H-pyrido[2,1-b]quinazolin-2-yl)propionic acid, m.p. 214° (acetic acid), is obtained from 2-bromo-5-fluoropyridine (prepared according to R. A. Abramovitch et al., J. Org. Chem. 39: 1802 [1974]) and 2-(4-amino-3-carboxyphenyl)propionic acid.

EXAMPLE 7

Under the conditions of Example 3(a), the methyl ester of 2-(6,8-dichloro-11-oxo-11H-pyrido[2,1-b]quinazolin-2-yl)propionic acid, m.p. 138° (ether-acetonitrile) is obtained from 2-bromo-3,5-dichloropyridine (prepared from 2-amino-3,5-dichloropyridine according to Example 4[b]) and the methyl ester of 2-(4-amino-3-carboxyphenyl)propionic acid.

EXAMPLE 8

A mixture of 1.4 g. of 2-(6,8-dichloro-11-oxo-11H-pyrido[2,1-b]quinazolin-2-yl)propionic acid methyl ester, 10 ml. of water, and 10 ml. of concentrated sulfuric acid is stirred for 4 hours at 120° (bath temperature). After cooling, the mixture is diluted with 10 ml. of ice water and adjusted with sodium hydroxide solution to a pH of 4-5. After extraction with ethyl acetate, drying, and concentration of the organic phase, 1.1 g. of 2-(6,8-dichloro-11-oxo-11H-pyrido[2,1-b]quinazolin-2-yl)propionic acid is obtained, m.p. 241° (dimethylformamide-water).

EXAMPLE 9

(a) Under the conditions of Example 3(a), the methyl ester of 2-(7-methyl-11-oxo-11H-pyrido[2,1-b]quinazolin-2-yl)propionic acid, m.p. 120° (acetonitrile) is obtained from 2-chloro-4-methylpyridine and the methyl ester of 2-(4-amino-3-carboxyphenyl)propionic acid.

(b) This ester product is hydrolyzed, under the conditions of Example 8, to 2-(7-methyl-11-oxo-11H-pyrido[2,1-b]quinazolin-2-yl)propionic acid, m.p. 267° (acetic acid).

EXAMPLE 10

(a) Under the conditions of Example 3(a), the methyl ester of 2-(9-methyl-11-oxo-11H-pyrido[2,1-b]quinazolin-2-yl)-propionic acid is obtained from 2-chloro-6-methylpyridine and the methyl ester of 2-(4-amino-3-carboxyphenyl)propionic acid.

(b) This ester product is hydrolyzed to 2-(9-methyl-11-oxo-11H-pyrido[2,1-b]quinazolin-2-yl)propionic acid under the conditions of Example 8.

EXAMPLE 11

(a) Under the conditions of Example 3(a), the methyl ester of 2-(8-methyl-11-oxo-11H-pyrido[2,1-b]quinazolin-2-yl)propionic acid, m.p. 151° (acetonitrile) is obtained from 2-bromo-5-methylpyridine and 2-(4-amino-3-carboxyphenyl)propionic acid methyl ester.

(b) This ester product is hydrolyzed under the conditions of Example 8 to 2-(8-methyl-11-oxo-11H-pyrido[2,1-b]quinazolin-2-yl)propionic acid, m.p. 233° (acetonitrile).

EXAMPLE 12

Under the conditions of Example 3(a), 2-(8-trifluoromethyl-11-oxo-11H-pyrido[2,1-b]quinazolin-2-yl)propionic acid is obtained from 2-bromo-5-trifluoromethylpyridine and 2-(4-amino-3-carboxyphenyl)propionic acid.

EXAMPLE 13

(a) Under the conditions set forth in Example 3(a), the methyl ester of 2-(9-methyl-7-trifluoromethyl-11-oxo-11H-pyrido[2,1-b]quinazolin-2-yl)propionic acid is obtained from 2-chloro-6-methyl-4-trifluoromethylpyridine (prepared according to S. Portnoy, J. Het. Chem.

6: 223 [1969]) and the methyl ester of 2-(4-amino-3-carboxyphenyl)propionic acid.

(b) This ester product yields, after hydrolyzing under the conditions of Example 8, 2-(9-methyl-7-trifluoromethyl-11-oxo-11H-pyrido[2,1-b]quinazolin-2-yl)propionic acid, m.p. 232° (acetonitrile).

EXAMPLE 14

(a) Under the conditions of Example 3(a), the methyl ester of 2-(8-bromo-7-methyl-11-oxo-11H-pyrido[2,1-b]quinazolin-2-yl)propionic acid, m.p. 150° (acetonitrile), is obtained from 2,5-dibromo-4-methylpyridine and the methyl ester of 2-(4-amino-3-carboxyphenyl)propionic acid.

(b) This ester product yields 2-(8-bromo-7-methyl-11-oxo-11H-pyrido[2,1-b]quinazolin-2-yl)propionic acid, m.p. 265° (acetic acid) by hydrolysis under the conditions of Example 8.

EXAMPLE 15

Under the conditions of Example 3(a), 2-(8-chloro-6-methyl-11-oxo-11H-pyrido[2,1-b]quinazolin-2-yl)propionic acid, m.p. 226° (dimethylformamide-water), is obtained from 2,5-dichloro-3-methylpyridine and 2-(4-amino-3-carboxyphenyl)propionic acid.

EXAMPLE 16

Under the conditions of Example 3(a), 5.2 g. of the methyl ester of 2-(4-amino-3-carboxyphenyl)propionic acid is reacted with 4.7 g. of 2-bromo-5-methylthiopyridine and worked up, thus obtaining 3.3 g. of the methyl ester of 2-(8-methylthio-11-oxo-11H-pyrido[2,1-b]quinazolin-2-yl)propionic acid, m.p. 113°–114° (diethyl ether).

EXAMPLE 17

1.3 g. of the methyl ester of 2-(8-methylthio-11-oxo-11H-pyrido[2,1-b]quinazolin-2-yl)propionic acid is saponified as described in Example 8 and worked up, thus obtaining 1.0 g. of 2-(8-methylthio-11-oxo-11H-pyrido[2,1-b]quinazolin-2-yl)propionic acid, m.p. 213°–214° (dimethylformamide-water).

EXAMPLE 18

190 mg. of 2-(8-methylthio-11-oxo-11H-pyrido[2,1-b]quinazolin-2-yl)propionic acid is combined with 10 ml. of glacial acetic acid and 5 ml. of chloroform. The mixture is mixed with 70 mg. of 30% hydrogen peroxide and agitated for two days at room temperature. Then another 7 mg. of 30% hydrogen peroxide is added to the mixture and the latter is stirred for one more day. The reaction mixture is concentrated under vacuum, the residue is recrystallized from methanol, and the yield is 140 mg. of 2-(8-methylsulfinyl-11-oxo-11H-pyrido[2,1-b]quinazolin-2-yl)propionic acid, m.p. 225°–226°.

EXAMPLE 19

Under the conditions of Example 18, 2.85 g. of the methyl ester of 2-(8-methylthio-11-oxo-11H-pyrido[2,1-b]quinazolin-2-yl)propionic acid is oxidized and worked up, thus obtaining 2.2 g. of the methyl ester of 2-(8-methylsulfinyl-11-oxo-11H-pyrido[2,1-b]quinazolin-2-yl)propionic acid, m.p. 160°–162° (methanol).

EXAMPLE 20

1.1 g. of the methyl ester of 2-(8-methylsulfinyl)-11-oxo-11H-pyrido[2,1-b]quinazolin-2-yl)propionic acid is combined with 20 ml. of polyphosphoric acid, heated to 80°, mixed in incremental portions with 335 mg. of sodium azide, and stirred for 8 hours at 80° and for 16 hours at room temperature.

The reaction mixture is then diluted with water, neutralized with concentrated ammonia, saturated with sodium chloride, and extracted with ethyl acetate. The organic phase is concentrated, the residue is recrystallized from methanoldiisopropyl ether, and the yield is 660 mg. of the methyl ester of 2-(8-methylsulfonimidoyl-11-oxo-11H-pyrido[2,1-b]quinazolin-2-yl)propionic acid, m.p. 158°–160°.

EXAMPLE 21

530 mg. of the methyl ester of 2-(8-methylsulfonimidoyl-11-oxo-11H-pyrido[2,1-b]quinazolin-2-yl)propionic acid is hydrolyzed under the conditions of Example 8 and worked up, thus obtaining 330 mg. of 2-(8-methylsulfonimidoyl-11-oxo-11H-pyrido[2,1-b]quinazolin-2-yl)propionic acid, m.p. 140°–150° (tetrahydrofuran-hexane) (dec.).

EXAMPLE 22

(a) 1.6 g. of 6-chloronicotinic acid, 2.2 g. of the methyl ester of 2-(4-amino-3-carboxyphenyl)propionic acid, and 20 mg. of potassium iodide are combined with 4 ml. of glycol dimethyl ether and stirred under argon for 6 hours at 150°. The reaction mixture is extensively concentrated under vacuum and combined with ethanol, yielding 750 mg. of the methyl ester of 2-(8-carboxy-11-oxo-11H-pyrido[2,1-b]quinazolin-2-yl)propionic acid as a crude product.

(b) 120 mg. of the thus-obtained crude product is saponified as described in Example 8 and worked up, thus producing 67 mg. of 2-(8-carboxy-11-oxo-11H-pyrido[2,1-b]quinazolin-2-yl)propionic acid, m.p. 318°–319°.

EXAMPLE 23

Under the conditions of EXAMPLE 3, 2-(8-bromo-11-oxo-11H-pyrido[2,1-b]quinazolin-2-yl)propionic acid methyl ester, having a melting point of 172° C. (methanol) was obtained from 2,5-dibromopyridine and 2-(4-amino-3-carboxyphenyl)propionic acid methyl ester.

EXAMPLE 24

Under the conditions of EXAMPLE 3, 2-(8-chloro-11-oxo-11H-pyrido[2,1-b]quinazolin-2-yl)propionic acid methyl ester (melting point 173° C. (ether)) was obtained from 2-bromo-5-chloropyridine and 2-(4-amino-3-carboxyphenyl)propionic acid methyl ester.

EXAMPLE 25

Under the conditions of EXAMPLE 3, 2-(8-fluoro-11-oxo-11H-pyrido[2,1-b]quinazolin-2-yl)propionic acid methyl ester, having a melting point of 138° C. (ether) was obtained from 2-bromo-5-fluoropyridine and 2-(4-amino-3-carboxyphenyl)propionic acid methyl ester.

EXAMPLE 26

Under the conditions of EXAMPLE 3, 2-(8-mesylamino-11-oxo-11H-pyrido[2,1-b]quinazolin-2-yl)propionic acid methyl ester, having a melting point of 209° C. (toluene) was obtained from 2-bromo-5-mesylaminopyridine and 2-(4-amino-3-carboxyphenyl)propionic acid methyl ester.

EXAMPLE 27

100 mg of 2-(8-methylthio-11-oxo-11H-pyrido[2,1-b]quinazolin-2-yl)propionic acid were reacted under the conditions of EXAMPLE 18 with 250 mg of 30% hydrogen peroxide, thereby obtaining 45 mg of 2-(8-methylsulfonyl-11-oxo-11H-pyrido[2,1-b]quinazolin-2-yl)propionic acid having a melting point of 240° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pyrido[2,1-b]quinazolinone of the formula

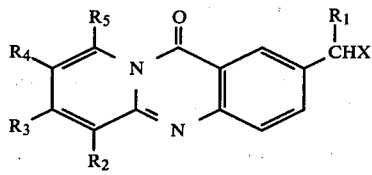

wherein
X is COOR wherein R is H, an alkali metal, an alkaline earth metal, Cu(II) or a methylglucamine cation;
$R_1$ is hydrogen or methyl; and
$R_2$ through $R_5$ are independently each hydrogen, trifluoromethyl, thiocyano, methylthio, methylsulfinyl, methylsulfonyl, methylsulfonimidoyl or methylsulfonamido, with the proviso that two or three of the groups $R_2$ through $R_5$ are hydrogen; or a salt thereof with a physiologically acceptable acid.

2. A method of achieving an anti-inflammatory effect in a mammal which comprises administering to the mammal an anti-inflammatorily effective amount of a composition comprising an anti-inflammatorily effective amount of a compound of the following formula and a pharmaceutically acceptable carrier,

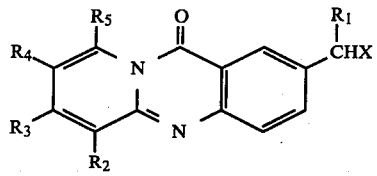

X is COOR wherein R is H, an alkali metal, an alkaline earth metal, Cu(II) or a methylglucamine cation;
$R_1$ is hydrogen or methyl; and $R_2$ through $R_5$ are independently each hydrogen, halogen, alkyl of 1-4 carbon atoms, trifluoromethyl, thiocyano, methylthio, methylsulfinyl, methylsulfonyl, methylsulfonimidoyl or methylsulfonamido, with the proviso that two or three of the groups $R_2$ through $R_5$ are hydrogen; or a salt thereof with a physiologically acceptable acid.

3. A method of claim 2, wherein one or two of groups $R_2$ through $R_5$ are fluorine, chlorine, bromine, methyl or trifluoromethyl.

4. 2-(8-Trifluoromethyl-11-oxo-11H-pyrido[2,1-b]quinazolin-2-yl)propionic acid, a compound of claim 1.

5. 2-(9-Methyl-7-trifluoromethyl-11-oxo-11H-pyrido[2,1-b]quinazolin-2-yl)propionic acid.

6. 2-(8-Methylthio-11-oxo-11H-pyrido[2,1-b]-quinazolin-2-yl)propionic acid, a compound of claim 1.

7. 2-(8-Methylsulfinyl-11-oxo-11H-pyrido[2,1-b]quinazolin-2-yl)propionic acid, a compound of claim 1.

8. 2-(8-Methylsulfonimidoyl-11-oxo-11H-pyrido[2,1-b]quinazolin-2-yl)propionic acid, a compound of claim 1.

9. A pharmaceutical composition comprising an anti-inflammatorily effective amount of a compound of claim 1 and a pharmaceutically acceptable carrier.

10. The pharmaceutical composition of claim 9 wherein the amount of active ingredient is 5–500 mg.

11. The pharmaceutical composition of claim 9 comprising one or two of said active ingredients.

12. 2-(8-methylsulfonyl-11-oxo-11H-pyrido[2,1-b]quinazoline-2-yl)propionic acid, a compound of claim 1.

* * * * *